United States Patent [19]

Silvestrini

[11] Patent Number: 5,278,183

[45] Date of Patent: Jan. 11, 1994

[54] METHOD FOR THE TREATMENT OF AUTOIMMUNE DISEASES

[75] Inventor: Bruno Silvestrini, Rome, Italy

[73] Assignee: Istituto Ricerca Francesco Angelini S.P.A., Rome, Italy

[21] Appl. No.: 868,311

[22] Filed: Apr. 14, 1992

[30] Foreign Application Priority Data

Apr. 22, 1991 [IT] Italy ........................................ 001101

[51] Int. Cl.$^5$ ............................................ A61K 31/415
[52] U.S. Cl. ........................................ 514/403; 514/825; 514/866; 514/885; 514/893
[58] Field of Search .............. 514/403, 825, 866, 885, 514/893

[56] References Cited

U.S. PATENT DOCUMENTS 4,999,367  2/1991  Balocchi et al. .................. 514/403
5,112,986  5/1992  Baiocchi et al. .................. 548/372

FOREIGN PATENT DOCUMENTS 0131317  1/1985  European Pat. Off. .
0191520  8/1986  European Pat. Off. .

OTHER PUBLICATIONS

Deodhar, Sharad D., "Autoimmune Diseases", *Immunology: Clinical, Fundamental, and Therapeutic Aspects*, VCH Publishers, New York, (1990) pp. 296–304.

European Search Report for Patent No. EP 92 20 1037.6, (Jul. 31, 1992).

Mastrantonio et al., "Interference of Two Anti-Inflammatory Drugs, Bendazac and Phenylbutazone, On The Cellular Kinetics of the Immune response", Ann. 1st. Super. Sonita (1973) 9: pp. 138–40.

Primary Examiner—Leonard Schenkman
Attorney, Agent, or Firm—Oblon, Spivak, McClelland, Maier & Neustadt

[57] ABSTRACT

A pharmaceutical composition for the treatment of autoimmune diseases comprising an effective amount of a compound of formula $$A-CH_2-O-CRR'-COOR''' \qquad (I)$$

where

A is the nucleus of 1-benzyl-indazol-3-yl,

R and R', the same or different from each other, are H or an alkyl having from 1 to 5 carbon atoms, R''' is H or an alkyl having from 1 to 4 carbon atoms, or, when R''' is H, of a salt thereof with organic or inorganic pharmaceutically acceptable bases.

4 Claims, No Drawings

METHOD FOR THE TREATMENT OF AUTOIMMUNE DISEASES

This invention relates to a pharmaceutical composition for the treatment of autoimmune diseases comprising a methoxy alkanoic acid of indazole as the active ingredient.

The European patent application A-0 382 276, describes a compound of formula $$A-CH_2-O-CRR'-COOR''' \qquad (I)$$

where

A is the nucleus of 1-benzyl-indazol-3-yl,
R and R', the same or different from each other, are H or an alkyl having from 1 to 5 carbon atoms,
R''' is H or an alkyl having from 1 to 4 carbon atoms, and, when R''' is H, the salts thereof with organic or inorganic pharmaceutically acceptable bases.

Moreover, the above patent application specifies that the compound of formula (I), even though it has some structural similarities with bendazac, it is different in as much as its pharmacological profile presents an analgesic activity absent in bendazac.

It has now been unexpectedly found that the compound of formula (I) is active even in the treatment of autoimmune diseases.

It is known that autoimmune diseases constitute a wide group of pathologies characterized by inflammation and destruction of tissues caused by the production, by the immune system, of antibodies against some constituents of its own organism. Examples of diseases considered to be of the autoimmune kind are rheumatoid arthritis, glomerulonephritis, Hashimoto's thyroiditis, systemic lupus erythematosus, myasthenia gravis, certain forms of hemolytic anemia, autoimmune thrombocytopenic purpura, certain hepatic disorders and type 1 diabetes.

It is also known that in the therapy of rheumatoid arthritis, which is one of the most frequent autoimmune diseases and therefore one of the most studied, have been utilized many steroidal and nonsteroidal anti-inflammatory drugs, some gold compounds, penicillin, immunodepressants and others. Aside from prevalently symptomatologic effects which can be obtained with numerous drugs in the acute phase, the most important effects are obtained with gold compounds and with penicillin but the latter cannot be administered for prolonged periods of time because it presents considerable and various toxic manifestations.

In turn, gold therapy induces a prolonged remission only in about 15% of the patients, it attenuates the symptomatology in 60-70% of the patients and, because of its toxicity, it must be suspended in 15-20% of the patients. After suspension of the gold therapy, the length of the remission is extremely variable (1-18 months). Although the recurrence is not usually so serious as the initial disease and the great majority of the patients responds favourably to a second cycle of gold therapy, many rheumatologists prefer to continue the therapy indefinitely without waiting for a relapse. After 3-6 years of continuous or discontinuous therapy, more than 50% of the patients who had initially responded (15%) must interrupt the therapy because of the relapse or because of the delayed toxicity. Moreover, there is also a high rate of quitting of the therapy because of the length of the treatment, the need for visits as an out patient and the laboratory tests. The gold therapy is not indicated in patients with nephropathy, hepatic disfunction or a medical history of infectious hepatitis or hematologic disorders (Goodman & Gilman "Le basi farmacologiche della terapia", 7th Italian ed., Zanichelli, p. 651-652).

Therefore, there is still a great need for a drug capable of inducing the arrest of the progression and, possibly, of also inducing the remission of rheumatoid arthritis, in particular, and of autoimmune diseases, in general, without causing serious side effects.

It is therefore an object of this invention to provide a pharmaceutical composition for the treatment of autoimmune diseases comprising an effective amount of a compound of formula $$A-CH_2-O-CRR'-COOR''' \qquad (I)$$

where

A is the nucleus of 1-benzyl-indazol-3-yl,
R and R', the same or different from each other, are H or an alkyl having from 1 to 5 carbon atoms,
R''' is H or an alkyl having from 1 to 4 carbon atoms, or, when R''' is H, of a salt thereof with organic or inorganic pharmaceutically acceptable bases, together with at least a pharmaceutically acceptable inert excipient.

A further object of this invention is to provide a method of treatment comprising administering to a patient in need of an anti-autoimmune agent an effective amount of a compound of formula $$A-CH_2-O-CRR'-COOR''' \qquad (I)$$

where

A is the nucleus of 1-benzyl-indazol-3-yl,
R and R', the same or different from each other, are H or an alkyl having from 1 to 5 carbon atoms,
R''' is H or an alkyl having from 1 to 4 carbon atoms, or, when R''' is H, of a salt thereof with organic or inorganic pharmaceutically acceptable bases.

Preferably, R''' is H while R=R'=methyl (the compound in which R''', R and R' have these meanings will indicated from now on with the code number F 2838).

Typical examples of autoimmune diseases which might benefit from the treatment with a pharmaceutical composition of this invention are: rheumatoid arthritis, glomerulonephritis, Hashimoto's thyroiditis, systemic lupus erythematosus, myasthenia gravis, autoimmune hemolytic anemia, autoimmune thrombocytopenic purpura, autoimmune disorders and type 1 diabetes.

Preferably, the pharmaceutical composition of this invention is prepared in a suitable dosage form comprising a dose effective in the treatment of an autoimmune disease of at least a compound of formula (I) or a salt thereof with a pharmaceutically acceptable base and at least an inert pharmaceutically acceptable excipient.

Examples of suitable dosage forms are tablets, capsules, coated tablets, granules, solutions and syrups for oral administration; ointments, creams and medicated patches for topic administration; suppositories for rectal administration and sterile solutions for injectable, aerosolic and ophthalmic administration.

The dosage forms may also contain other conventional ingredients as preservatives, stabilizers, surface-active agents, buffers, salts for the regulation of the osmotic pressure, emulsifiers, sweeteners, colouring agents, flavouring agents and the like.

When required by particular therapies, the pharmaceutical composition for the treatment of autoimmune diseases according to this invention may contain other pharmacologically active ingredients whose concomitant administration is therapeutically useful.

The amount of the compound of formula (I) or of a salt thereof with organic or inorganic pharmaceutically acceptable bases in the pharmaceutical composition of this invention may vary in a rather wide range depending on known factors such as, for instance, the type of autoimmune disease to be treated, the severity of the disease, the body weight of the patient, the dosage form, the chosen route of administration, the number of dosage forms administered daily and the efficacy of the chosen compound of formula (I). However, the optimum amount may be easily and routinely determined by a person skilled in the art.

Typically, the amount of the compound of formula (I) or of a salt thereof with organic or inorganic pharmaceutically acceptable bases in the pharmaceutical composition for the treatment of autoimmune diseases of this invention, will be such that it insures an administration level of from 0.01 to 100 mg/Kg/day. For instance, in the case of oral administration tablets dosed at from 0.03 to 1 g will be administered several times a day while in the case of ophthalmic administration a sterile solution dosed at from 0.5 to 2% will be used, that too several times a day.

The dosage forms of the pharmaceutical composition of this invention can be prepared according to techniques which are known to the pharmaceutical chemist and comprise procedures such as mixing, granulation, compression, solubilization and sterilization.

AF 2838 has been studied on an experimental disease of the rat which presents an autoimmune phase (Freund's adjuvant arthritis). During the course of this experimentation, the electrophoretic behaviour of albumin in the blood has been specifically studied since previous studies (Silvestrini B. et al., Can. J. Biochem., Loc. cit.) had shown that in the course of inflammatory diseases the reduction of albumin in the blood is partly due to denaturation with loss of the elecrophoretic characteristics.

AF 2838 has been administered in a diet at 0.5% because this dose assures an essentially constant concentration in the blood of 100 microg/ml.

Since there exist no other pharmaceutical compositions having a pharmacological profile similar to that of AF 2838, the comparison has been carried out with indomethacin administered at a known effective dosage (1 mg/Kg). In any case this comparison has been considered useful to compare the efficacy of the final therapeutic effect and to evaluate the ability of AF 2838 to improve the course of the disease via interference with body fluids parameters, such as serum albumin concentration, which do not represent the objective of indomethacin.

More specifically, 0.05 ml of a suspension (5 mg/ml) of M. Tuberculolosis (H37Ra-Difco) in a very fluid paraffin (Merck 7174) have been injected in the right posterior paw of male rats according to Newbold B. B. (Chemotherapy of arthritis induced in rats by mycobacterial adjuvant, Brit. J. Pharmacol. 21, 127–136, 1963) except that the volume of the paw has been measured with a pletismometer model 7150 by Ugo Basile, Cernerio, Varese, Italy.

Groups of 5 animals each from different groups under observation have been sacrificed on the second day after injection of adjuvant and then weekly for 6 weeks.

The erythrocyte sedimentation rate (ESR) has been measured according to Westergren (Douglas A. N., Basic Methodology, In: Clinical Diagnosis and Management by Laboratory Methods, eds. Todd, Sanford, Davidsohn; W. B. Saunders Company, Philadelphia, vol. 1, pp. 858-915, 1979). Total plasma proteins have been determined according to Lowry O. H. et al. (Protein measurement with folin phenol reagent, J. Biol. Chem., 193:265-275, 1951). The electrophoresis of the plasma proteins has been carried out in a Mc Ilveine buffer (pH 7.0; I 0.2) on strips of cellulose acetate (2.5*16an).

Six animals in each treated group have been kept under observation until day 51 after the injection of adjuvant; at different intervals the body weight, the food intake and the volume of the paw have been measured.

The results are shown in the following tables.

TABLE I

Freund's adjuvant arthritis
increase in the volume of the paw (ml)

| time (days) | arthritic controls | AF 2838 (0.5% of diet) | indomethacin (1 mg/Kg orally) | normal controls |
|---|---|---|---|---|
| 5 | 1.36 ± 0.17 | 1.35 ± 0.12 | 1.03 ± 0.06** | 0.77 ± 0.04 |
| 23 | 2.16 ± 0.25 | 1.52 ± 0.40* | 1.02 ± 0.12** | 0.99 ± 0.04 |
| 44 | 2.59 ± 0.60 | 1.32 ± 0.45** | 0.90 ± 0.08** | 0.89 ± 0.04 |

* = p lower than 0.05 (analysis of variance)
** = p lower than 0.01 (analysis of variance)

TABLE II

Freund's adjuvant arthritis
reduction in serum albumin (ml/ml)

| time (days) | arthritic controls | AF 2838 (0.5% of diet) | indomethacin (1 mg/Kg orally) | normal controls |
|---|---|---|---|---|
| 2 | 13.99 ± 3.20 | 17.02 ± 3.13 | 15.83 ± 3.39 | 21.11 ± 2.31 |
| 23 | 12.95 ± 1.92 | 18.40 ± 2.57* | 16.98 ± 2.29 | 20.72 ± 1.45 |
| 44 | 7.80 ± 2.15 | 26.16 ± 4.29** | 25.49 ± 1.63** | 26.07 ± 0.74 |

* = p lower than 0.05 (analysis of variance)
** = p lower than 0.01 (analysis of variance)

TABLE III

Freund's adjuvant arthritis
increase in the erothrocyte sedimentation rate (mm/2h)

| time (days) | arthritic controls | AF 2838 (0.5% of diet) | indomethacin (1 mg/Kg orally) | normal controls |
|---|---|---|---|---|
| 2 | 5.2 ± 1.30 | 5.2 ± 3.83 | 7.8 ± 2.28 | 1.8 ± 0.45 |
| 23 | 14.2 ± 4.42 | 6.6 ± 7.99 | 4.4 ± 4.93 | 1.0 ± 0.0 |
| 44 | 34.2 ± 17.25 | 3.5 ± 5.00** | 1.0 ± 0.??** | 1.0 ± 0.0 |

** = p lower than 0.01 (analysis of variance)

TABLE IV

Freund's adjuvant arthritis
changes in body weight (g)

| time (days) | arthritic controls | AF 2838 (0.5% of diet) | indomethacin (1 mg/Kg orally) | normal controls |
|---|---|---|---|---|
| 2 | 182.3 ± 7.58 | 186.2 ± 6.52 | 185.2 ± 5.91 | 199.7 ± 07.45 |
| 23 | 191.2 ± 29.98 | 247.8 ± 21.46* | 255.5 ± 38.87** | 316.5 ± 23.45 |
| 44 | 254.5 ± | 334.7 ± 31.61* | 329.8 ± 35.62* | 393.3 ± |

TABLE IV-continued

| | Freund's adjuvant arthritis changes in body weight (g) | | | |
|---|---|---|---|---|
| time (days) | arthritic controls | AF 2838 (0.5% of diet) | indomethacin (1 mg/Kg orally) | normal controls |
| | 57.27 | | | 37.10 |

\* = p lower than 0.05 (analysis of variance)
\*\* = p lower than 0.01 (analysis of variance)

The above results show that AF 2838 is inactive on the primary inflammation (first 5 days); in contrast, its effect on the paw volume becomes apparent during the secondary inflammation (at about 23 days as a manifestation of diffuse autoimmune reaction). At the same time (23 days), it becomes also apparent its protecting effect on serum albumin.

On the contrary, the first effect shown by indomethacin is an anti-inflammatory activity on primary lesions (reduction of the volume of the paw already at 5 days from the adjuvant infection) while the increase in serum albumin is obtained only at 44 days.

With both products the erythrocyte sedimentation rate tends to decrease in the final phases of the experimental stage as an index of healing.

Contrary to what happens with immunodepressants of the conventional type, with which one observes a reduction of the body weight superior to that which occurs in arithritic controls (Billingham M. E. J., Models of arthritis and the search for anti-arthritic drugs; Pharmc. Ther., 21: 389-428, 1983), the effect on the body weight demonstrates that control of the disease with AF 2838 is not obtained to the detriment of the health conditions of the animals treated.

Further tests with increasing oral doses up to 400 mg/Kg showed that of AF 2838 has no activity on edema from carrageenin (comparison drugs: indomethacin active at 0.5 mg/Kg orally, phenylbutazone active at 12.5 mg/Kg orally and acetylsalicylic acid active at 25 mg/Kg orally), antipyretic activity (test: fever caused by yeast; comparison drugs: acetylsalicylic acid active at less than 100 mg/Kg orally and aminopyrine active at less than 50 mg/Kg orally), antigranuloma activity (test: granuloma from cotton pellets; comparison drug: hydrocortisone active at 25 mg/Kg ip), lymphocytic activity (test: involution of the thymus; comparison drug: hydrocortisone active at less than 25 mg/Kg ip), and ulcer healing activity (comparison drug: phenyl butazone active at less than 75 mg/Kg orally).

The lack of activity on the above mentioned tests seems to suggest that AF 2838 does not interfere with the metabolism of arachidonic acid both at the level of the periferic tissue and of the central nervous system.

Furthermore, increasing quantities of AF 2838 up to 200 microg/ml have no inhibition on the cyclo-oxygenase system of seminal vesticles of the ram; comparison drug: indomethacin (active at less than 0.4 microg/ml) and on the 5-lipoxygenase system of leucemic basophils in the rat with comparison compound: nordihydroguaiaretic acid (active at 0.3 microg/ml).

In the course of the evaluation of the pharmacolgal profile of AF 2838 the effects on the immune reactions of the mouse have also been studied: it has resulted to be inactive both at the cellular and the humoral level up to a dose of 200 mg/Kg. Moreover, it has shown inhibitory effects on the proliferative responces of T and B lymphocytes to specific mytogens (concanavelin A and lipopolysaccharides respectively).

Toxycological studies have shown that the minimal toxic doses of AF 2838 in the mouse and in the rat are of 400 mg/Kg intraperitoneally and of 800 mg/Kg orally. AF 2838 has resulted to be without alpha, beta, $H_1$, $H_2$, blocking effects as well as anticholinergic activity. The antibradychinin activity has appeared only at very elevated doses (20 mg/Kg intravenously) and it has resulted to be more than 20 times inferior to that of phenylbutazone while the antiserotoninic activity in vitro has appeared only at concentrations of 10 microg/ml and it has resulted to be of about 5000 times inferior to that of the comparison drug (cyproheptadine).

The profile of AF 2838 which results from the studies reported above makes it a prototype of a specific drug for the treatment of anti-immune diseases active even orally and without anti-inflammatory activity and toxic effects characteristic of aspirin-like drugs, of immunosuppressant activity and of important side effects which might limit its administration in terms of dosage or length of treatment.

The other compounds of formula (I) possess a similar profile.

I claim:

1. A method of treatment comprising administering to a patient in need of an anti-autoimmune agent an effective amount of a compound of formula

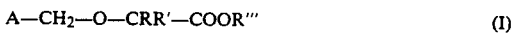

$$A-CH_2-O-CRR'-COOR''' \qquad (I)$$

where A is the nucleus of 1-benzyl-indazol-3-yl,

R and R', the same or different from each other, are H or an alkyl having from 1 to 5 carbon atoms, R''' is H or an alkyl having from 1 to 4 carbon atoms, or, when R''' is H, of a salt thereof with organic or inorganic pharmaceutically acceptable bases.

2. A method of treatment according to claim 1, wherein the patient in need of an anti-autoimmune agent is suffering from rheumatoid arthritis, glomerulonephritis, Hashimoto's thyroiditis, systemic lupus erythematosus, myasthenia gravis, autoimmune hemolytic anemia, autoimmune thrombocytopenic purpura, autoimmune hepatic disorders or type 1 diabetes.

3. The method according to claim 1, wherein said compound of formula (I) is administered by systemic route in a dosage form of from 30 to 1000 mg.

4. The method according to claim 1, wherein said compound of formula (I) is administered as an ophthalmic composition comprising a sterile solution of from 0.5 to 2% of the compound of formula (I).

* * * * *